US009649225B2

(12) United States Patent
Kirsch et al.

(10) Patent No.: US 9,649,225 B2
(45) Date of Patent: *May 16, 2017

(54) ELECTRONIC HEARING PROTECTOR WITH QUADRANT SOUND LOCALIZATION

(71) Applicant: HARMAN INTERNATIONAL INDUSTRIES, INC., Stamford, CT (US)

(72) Inventors: James M. Kirsch, Salt Lake City, UT (US); Jeffrey L. Hutchings, Lehi, UT (US); Russell Lambert, Salt Lake City, UT (US); Josh Hunsaker, Logan, UT (US)

(73) Assignee: HARMAN INTERNATIONAL INDUSTRIES, INC., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/918,866

(22) Filed: Oct. 21, 2015

(65) Prior Publication Data
US 2016/0038343 A1 Feb. 11, 2016

Related U.S. Application Data

(63) Continuation of application No. 14/063,820, filed on Oct. 25, 2013, now Pat. No. 9,180,055.

(51) Int. Cl.
*A61F 11/14* (2006.01)
*H04R 5/027* (2006.01)
(Continued)

(52) U.S. Cl.
CPC ............ *A61F 11/14* (2013.01); *H04R 1/1083* (2013.01); *H04R 5/027* (2013.01);
(Continued)

(58) Field of Classification Search
None
See application file for complete search history.

(56) References Cited

U.S. PATENT DOCUMENTS 3,952,158 A * 4/1976 Kyle ................. H04R 3/04
381/372
4,985,925 A * 1/1991 Langberg ........... G10K 11/1788
381/71.13
(Continued)

OTHER PUBLICATIONS

Extended European Search Report for Application No. 14190105.8 dated Mar. 13, 2015.
(Continued)

*Primary Examiner* — Paul Huber
(74) *Attorney, Agent, or Firm* — Artegis Law Group, LLP (57) ABSTRACT

An electronic hearing protector includes an ear cup assembly comprising a front exterior microphone that provides a front microphone signal and a rear exterior microphone that provides a rear microphone signal. A processor receives and digitizes the front microphone signal and the rear microphone signal, and provides a front channel signal and a rear channel signal indicative thereof respectively. A filter receives the rear channel signal and has a cut-off frequency value that provides a high-frequency roll-off and a notch at a notch filter frequency value that is less than the cut-off frequency value, where the filter provides a filtered signal. A first signal indicative of the front channel signal and a second signal indicative of the filtered signal are summed, and a signal indicative of the summed signal is provided to a speaker within the ear cup that provides an audio signal within the first ear cup indicative of the summed signal.

20 Claims, 10 Drawing Sheets

(51) Int. Cl.
    H04R 1/10        (2006.01)
    H04R 3/00        (2006.01)
    H04R 5/033       (2006.01)

(52) U.S. Cl.
    CPC ....... *A61F 2011/145* (2013.01); *H04R 1/1008* (2013.01); *H04R 3/005* (2013.01); *H04R 5/033* (2013.01); *H04R 2410/05* (2013.01)

(56) References Cited

U.S. PATENT DOCUMENTS

| | | | | |
|---|---|---|---|---|
| 8,774,421 B2* | 7/2014 | Kimura | ............... | H04R 1/1083 379/406.03 |
| 2003/0169891 A1* | 9/2003 | Ryan | ............... | H04R 1/08 381/92 |
| 2007/0225035 A1* | 9/2007 | Gauger | ............... | H04M 1/6066 455/553.1 |
| 2010/0296666 A1* | 11/2010 | Lin | ............... | G10K 11/178 381/71.6 |
| 2011/0200203 A1* | 8/2011 | Chu | ............... | H04R 3/007 381/74 |
| 2012/0278070 A1* | 11/2012 | Herve | ............... | G10L 21/0208 704/226 |
| 2013/0129105 A1* | 5/2013 | Hua | ............... | H04R 1/1083 381/71.6 |
| 2013/0243214 A1* | 9/2013 | Penketh | ............... | G10K 11/175 381/71.6 |
| 2013/0301844 A1* | 11/2013 | Konchitsky | ............... | H04R 3/002 381/71.1 |
| 2014/0185849 A1* | 7/2014 | Ma | ............... | H04R 25/453 381/318 |
| 2014/0348360 A1* | 11/2014 | Gran | ............... | H04R 25/50 381/318 |

OTHER PUBLICATIONS

"Listen HTRF Database", http://recherche.ircam.fr/equipes/salles/listen/ Institut De Recherche Et Coordination Acoustique/Musique, 2003.

Welch, "The Use of Fast Fourier Transform for Estimation of Power Spectra: A Method Based on Time Averaging Oven Short, Modified Periodograms", IEE Trans. Audio Electroacoustics, vol. AU-15, Jun. 1967, pp. 70-73.

* cited by examiner

ELECTRONIC HEARING PROTECTOR WITH QUADRANT SOUND LOCALIZATION

CROSS-REFERENCE TO RELATED APPLICATIONS

This application is a continuation of the co-pending U.S. patent application titled, "ELECTRONIC HEARING PROTECTOR WITH QUADRANT SOUND LOCALIZATION," filed on Oct. 25, 2013 and having Ser. No. 14/063,820. The subject matter of this related application is hereby incorporated herein by reference.

FIELD OF TECHNOLOGY

The present disclosure relates to the field of electronic hearing protection, and in particular to electronic hearing protectors that include quadrant sound localization.

RELATED ART

Humans (and other animals) use two ears to localize sounds from left to right and from front to back. A sound source at a given angle will arrive at the closer ear earlier and typically at a stronger level, and will arrive at the farther ear later and typically at a weaker level. These binaural cues are known as the interaural time difference (ITD) and the interaural intensity difference (IID). When a sound source is directly in front of the listener, the levels and arrival times are equal.

This simplification, referred to as "duplex theory", allows for localization of sounds in the horizontal plane in front of the listener, but there remains some ambiguity if sounds from the rear are also of interest. For example, a sound originating from a point directly ahead of the listener would have roughly the same ITD and IID as a sound originating from a point directly behind the listener at the same distance. In fact, shifting the sound source 30 degrees to the left in both the front and rear would result in a similar ambiguity. In other words, duplex theory is insufficient for front-to-back localization of sound, and also for localization in elevation. For every off-axis angle, there exists a set of points resembling a cone with an axis through both ears, known as the "cone of confusion", where a sound coming from anywhere on that cone will not be resolvable within that cone.

Additional factors beyond those identified by duplex theory allow for better localization of sound. Spectral shaping of sounds due to reflection and refraction around and along the head, torso, and outer ear (pinna) may be used to infer information about the location of the source. For example, a sound originating from behind the listener must travel through and around the tissue of the outer ear, or pinna, which will act as an acoustic filter. This filter will shape the spectrum of the original sound, which can be used by the brain as a cue to the location of the sound source. The characteristics of the various spectral cues encoded in a sound by the head, torso, and ears of a listener are known as head-related transfer functions (HRTF), and vary from person to person.

Modeling of spatial cues via HRTFs has been used to convert surround sound content to stereo, so that spatial information from a game or a movie is encoded within two channels. However, since HRTFs vary from person to person, a given HRTF measured and encoded for one listener may not always recreate a the correct spatial sensation for a different listener.

The localization problem may be simplified when the headphones have microphones directly on them (such as mounted on the hearing protector ear cup), so the listener can hear the environment instead of a recording or broadcast. Since the listener's head is already spatially filtering the incoming sound, fewer parts of the HRTF are needed, which will require less processing. Left/right panning is still distinguishable. However, the use of headphones still alters the listener's HRTF since normal pinna filtering is bypassed when a microphone is placed on the outside of the hearing protection ear cup.

Figure 1:
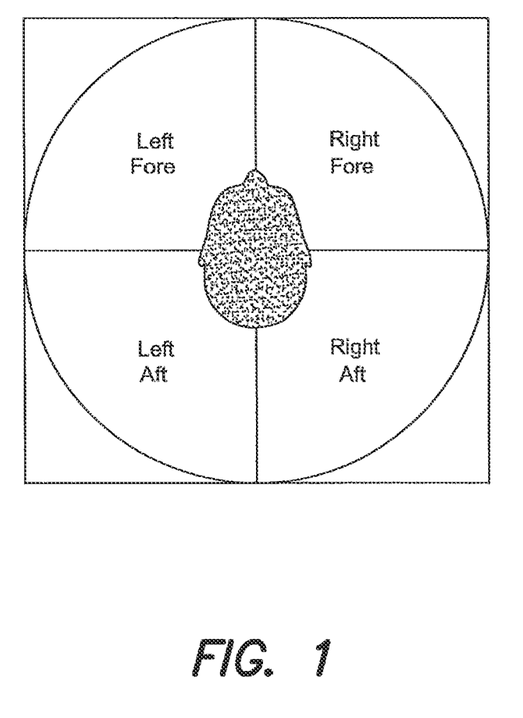
FIG. 1 is a pictorial illustration illustrating quadrants surrounding the head of a listener.
Figure 2A:
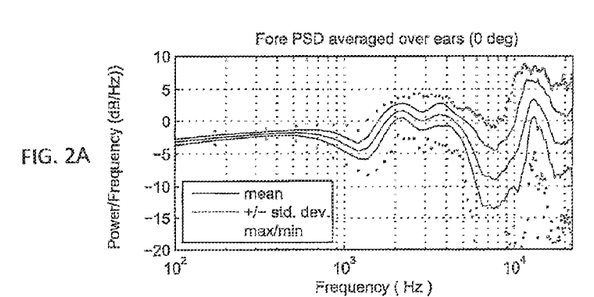
FIGS. 2A-2F illustrate plots of the average power spectral density for six different azimuth angles corresponding to sources in front of the listener.
Figure 2B:
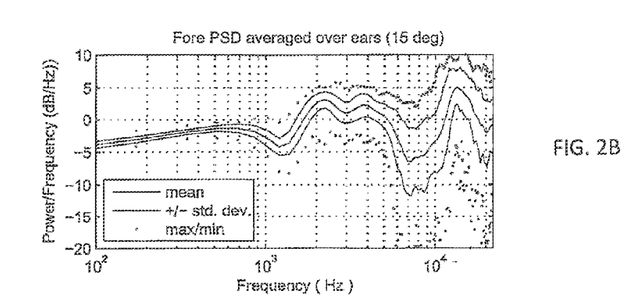
Figure 2C:
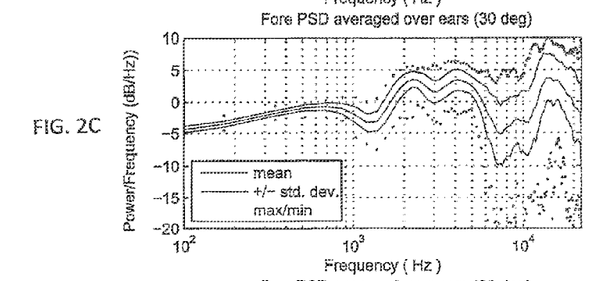
Figure 2D:
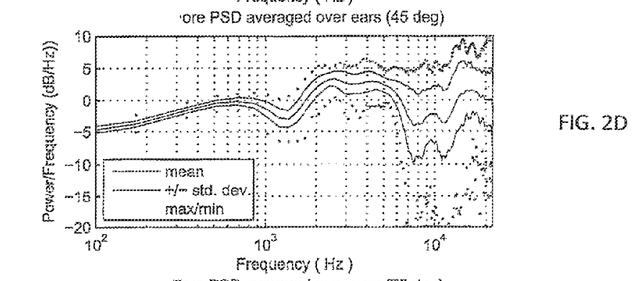
Figure 2E:
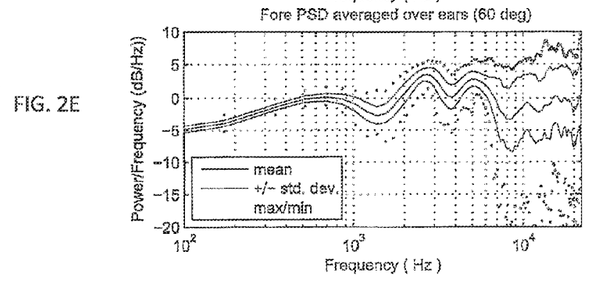
Figure 2F:
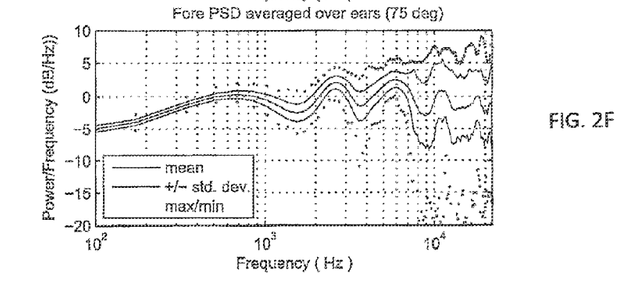

The localization problem can be further simplified by reducing the required resolution. Research has focused on the ability to distinguish closely spaced angles, e.g., 5° to 10°. Some sound localization applications require less angle resolution. Quadrant localization attempts to resolve confusion between sources that are fore versus aft, in addition to the left versus right localization that is natural to the head, as seen in FIG. 1.

Several efforts have been made to empirically measure individual HRTFs. The results of one such effort by AKG and IRCAM is available online See "*Listen HRTF Database*." http://recherche.ircam.fr/equipes/salles/listen/Institut De Recherche Et Coordination Acoustique/Musique, 2003. Last visited Oct. 23, 2013. This database contains the head-related impulse response (HRIR) of about fifty test subjects. Analysis of this data confirms the fact that HRTFs are specific to each individual, but it also shows that there are some common factors among most HRTFs.

The data provided contains an HRIR for each test subject at 187 combinations of azimuth and elevation angles. For the fore-aft localization problem only the HRIRs corresponding to sound sources in the horizontal plane (i.e., elevation angle=0) and on the ipsilateral side (the ear closer to the sound source) are of interest. For each ear, there are 13 such HRIRs, equally spaced by 15°. Given a stationary listener head, let 0° represent a point directly in front of the head. Similarly, 90° is directly left of the head, and 180° is directly behind the head. For simplicity, it is assumed that the head is symmetric and refer to all ears as if they were a left ear. In other words, 90° will always represent a point on the ipsilateral side; no distinction was made between left and right ears.

Any two points in the horizontal plane that share the same ITD and IID are referred to as "azimuth pairs." Such pairs occur at angle pairs of the form $\theta_{fore}=90°-\phi$, $\theta_{aft}=90°+\phi$ where $\phi$ is an arbitrary angle away from the ear. There are six possible azimuth pairs available in the database: 0°-180°, 15°-165°, 30°-150°, 45°-135°, 60°-120°, and 75°-105°.

For each of the 13 HRIRs of interest, an estimate of the spectral density using Welch's method was computed. See publication by Welch, P. D, entitled "*The Use of Fast Fourier Transform for the Estimation of Power Spectra: A Method Based on Time Averaging Over Short, Modified Periodograms*" IEEE Trans. Audio Electroacoustics, Vol. AU-15 (June 1967), pp. 70-73. Subtracting the spectrum of the test stimulus from the power spectral density of the HRIR shows the spectral shaping that occurs as a result of head geometry. It is assumed that, after compensation, the test stimulus had a flat frequency response, however the gain of the stimulus signal is unknown. This information is important for determining which frequencies are attenuated or amplified by the system. Without a reference signal, only the relative power of certain frequencies versus other frequencies can be seen. In this analysis, the reference signal was chosen, somewhat arbitrarily, to be a white signal at 30 dB.

Figure 3:
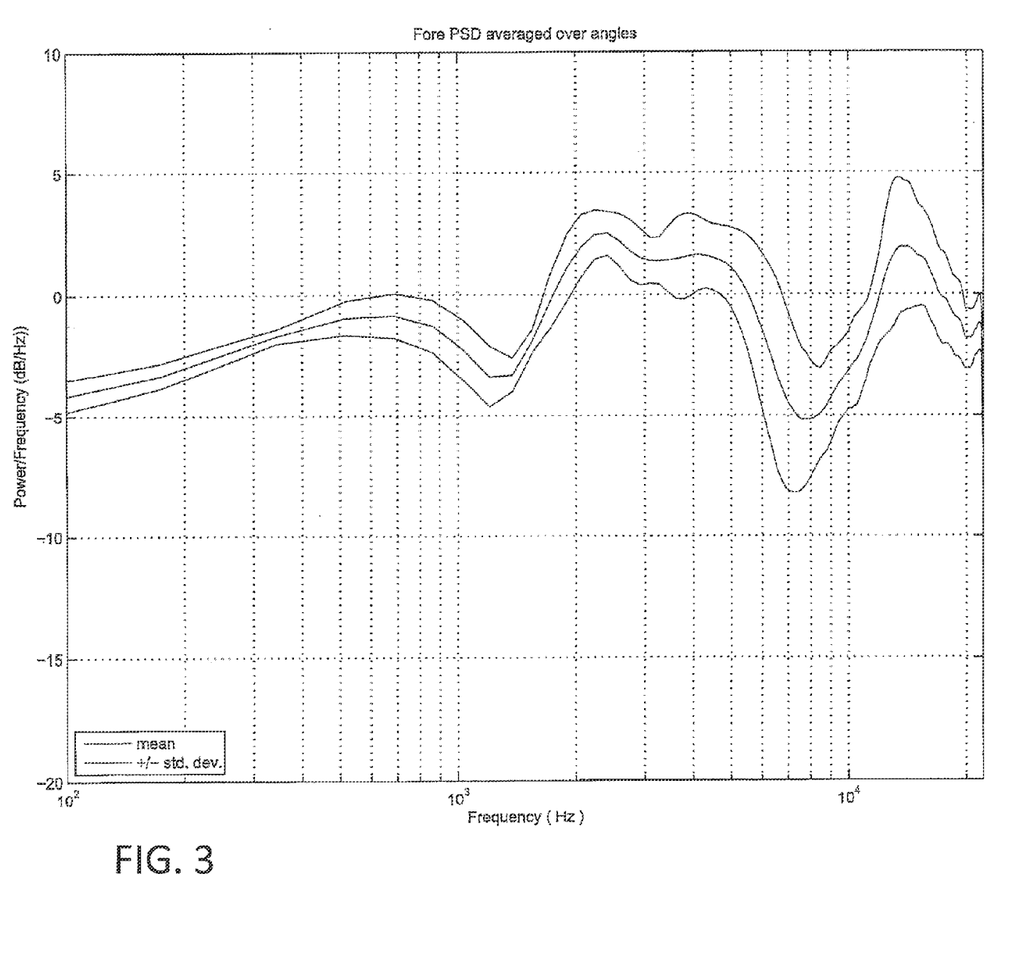
FIG. 3 illustrates a weighted average of the power spectral density over six forward azimuth angles illustrated in FIGS. 2A-2F.
Figure 4A:
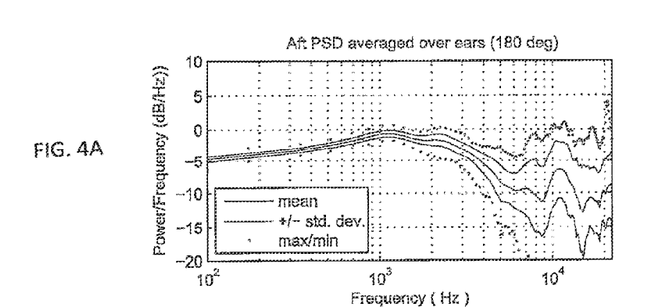
FIGS. 4A-4F illustrate plots of the average power spectral density over the test listener's ears for six different azimuth angles corresponding to sources aft of the listener.
Figure 4B:
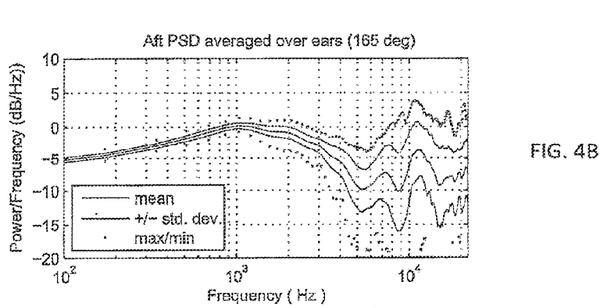
Figure 4C:
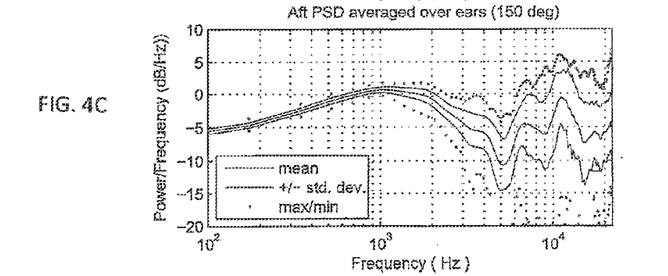
Figure 4D:
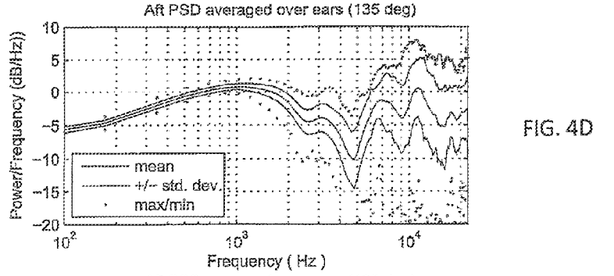
Figure 4E:
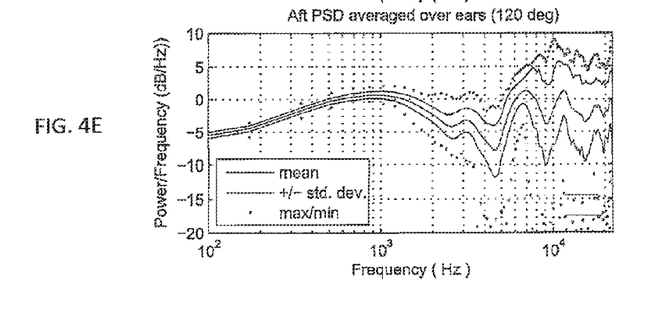
Figure 4F:
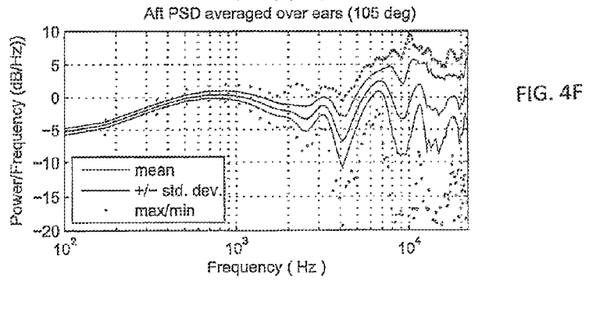
Figure 5:
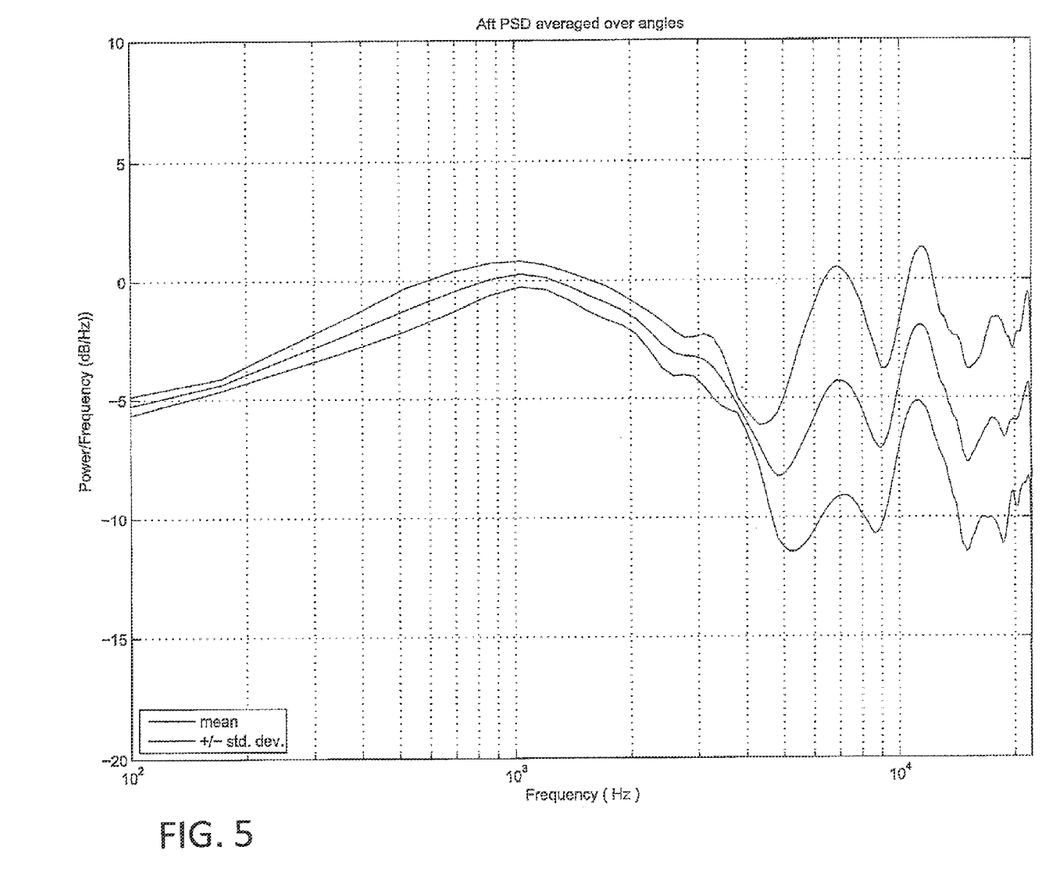
FIG. 5 illustrates a weighted average of the power spectral density over the six aft azimuth angles illustrated in FIGS. 4A-4F.
Figure 6A:
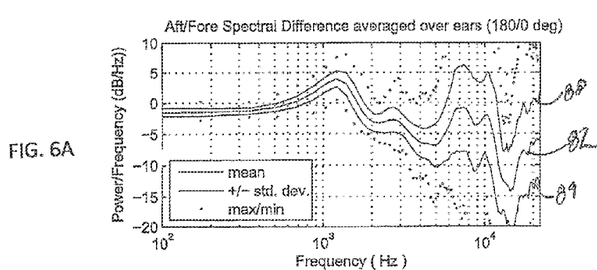
FIGS. 6A-6F illustrate the spectral differences for each of the six azimuth pairs set forth in FIGS. 2A-2F and FIG. 4A-4F.
Figure 6B:
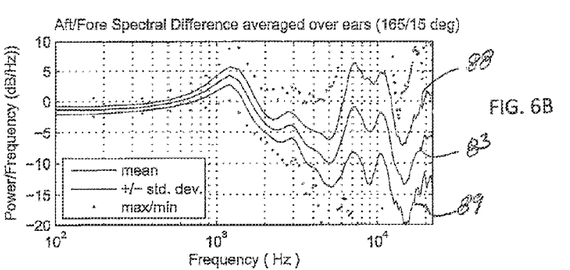
Figure 6C:
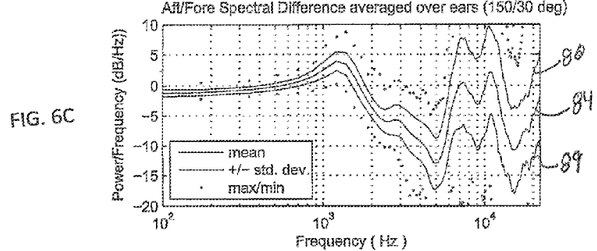
Figure 6D:
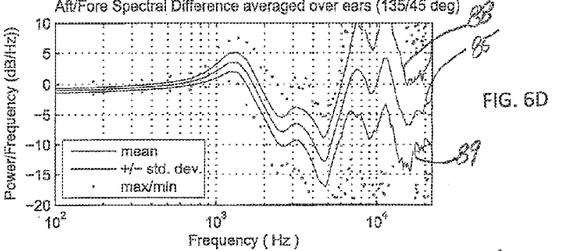
Figure 6E:
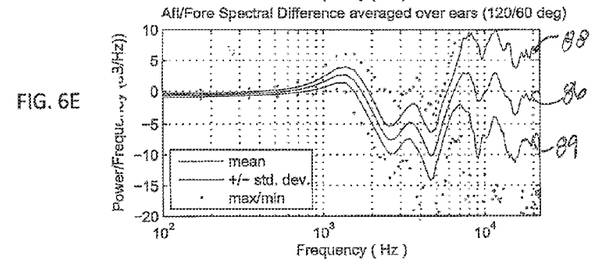
Figure 6F:
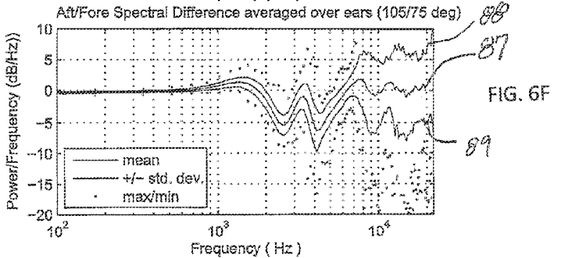

FIGS. 2A-2F show plots of the average power spectral density over the listener's ears for each of the six azimuth angles (e.g., 0 deg, 15 deg, 30 deg, 45 deg, 60 deg and 75 deg) corresponding to sound sources in front of the listener. FIG. 3 shows a weighted average of the power spectral density over the six forward azimuth angles. A weighting curve was applied that emphasizes angles closer to 0°. FIGS. 4A-4F show plots of the average power spectral density over the listener's ears for each of the six azimuth angles (e.g., 180 deg, 165 deg, 150 deg, 135 deg, 120 deg and 105 deg) corresponding to a sound sources behind the listener. FIG. 5 shows a weighted average of the power spectral density over the six rear azimuth angles. A weighting curve was applied that emphasizes angles closer to 180°.

A goal of this research is quadrant localization in the horizontal plane. Duplex theory is helpful by determining the azimuth position of a sound source. Whereas duplex theory takes advantage of binaural cues, aft-fore differentiation relies heavily on monaural cues. The spectral cues used to locate sounds can be detected by a single ear, and do not require simultaneous information from both ears. To eliminate the "cone of confusion," the spectral differences between two points in the cone are evaluated, specifically, in the points where the cone of confusion intersects the horizontal plane. The information encoded in these differences provide a key to quadrant localization.

Figure 7:
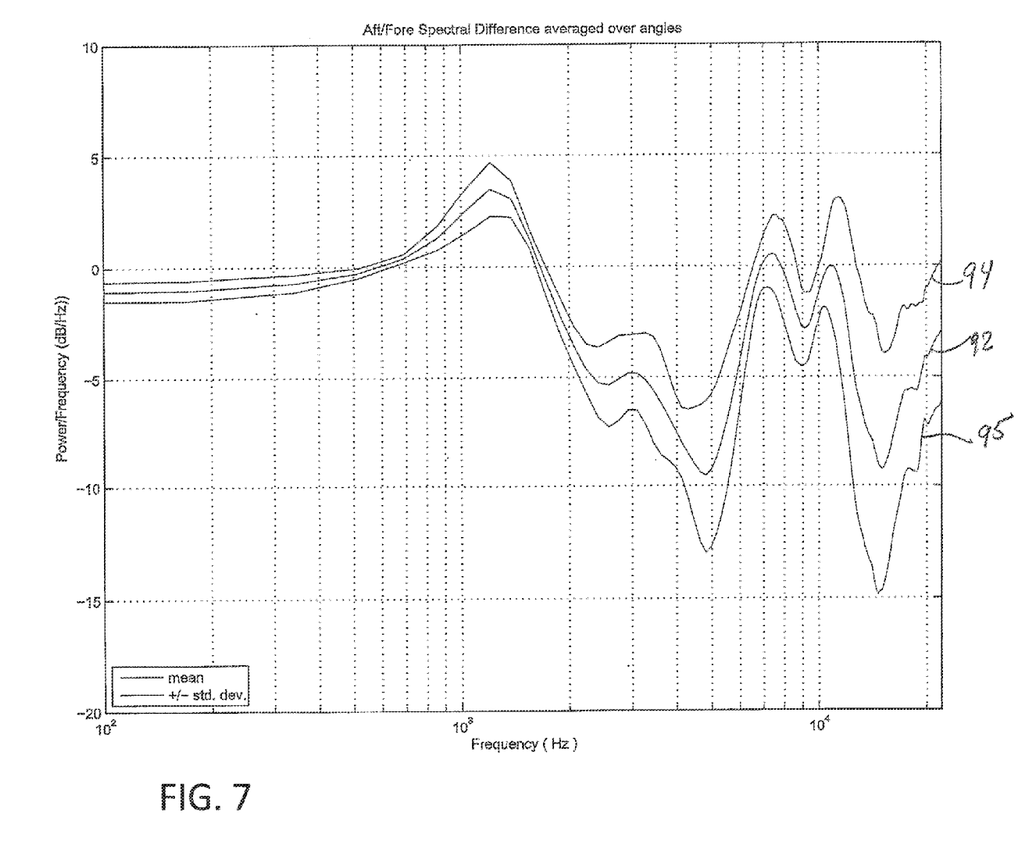
FIG. 7 shows the spectral differences averaged over all subject ears and all azimuth pairs.

FIGS. 6A-6F shows the spectral differences for each of the six azimuth pairs. Lines 82-87 represent the average spectral difference over all subject ears. Lines 88, 89 represent one standard deviation above and below the average associated, and the individual points in each plot represent point-wise max and mins. As can be seen, the differences are most pronounced where the angle difference increases. FIG. 7 shows the spectral differences averaged over all subject ears and all azimuth pairs on line 92, and lines 94, 95 represent one standard deviation above and below respectively.

There is a need for an improved electronic hearing protector with sound localization.

SUMMARY OF THE INVENTION

An electronic hearing protector includes an ear cup assembly comprising a front exterior microphone that provides a front microphone signal and a rear exterior microphone that provides a rear microphone signal. A processor receives the front microphone signal and rear microphone signal, and provides a front channel signal and a rear channel signal. A first filter, having a cut-off frequency value, receives the rear channel signal and provides a first filtered signal. A second filter, having a notch frequency value, receives the first filtered signal and provides a second filtered signal. A summer receives a first signal indicative of the front channel signal and a second signal indicative of the second filtered signal and provides a summed signal to a transducer that provides an audio signal within the first ear cup indicative of the summed signal that facilitates sound localization for the wearer of the electronic hearing protector.

The first filter may comprise a first biquad filter configured and arranged as a low-pass filter, and the second filter may comprise a second biquad filter configured and arranged as a notch filter.

The first biquad filter may have a cut-off frequency of about 12 kHz, and the second biquad filter may include a notch frequency located at about 4.9 kHz.

The processor may also receive a second front microphone signal and second rear microphone signal, and provide a second front channel signal and a second rear channel signal. A low pass filter receives the second rear channel signal and provides a second low pass filtered signal. A notch filter receives the second low pass filtered signal and provides a second notch filtered signal. A second summer receives a third signal indicative of the second front channel signal and a fourth signal indicative of the second notch filtered signal and provides a second summed signal to a second transducer that provides a second audio signal within the second ear cup indicative of the second summed signal.

The electronic hearing protector may also include front channel processing that includes a front channel shelf filter that receives the first front channel signal and provides a front channel filtered signal. A front channel notch filter receives the front channel filtered signal and provides the first signal.

The front channel shelf filter may comprise a biquad filter with a cut-off frequency of about 1.9 kHz. The front channel notch filter may comprise a second biquad filter with a notch of about 8.1 kHz.

In another embodiment, an electronic hearing protector includes an ear cup assembly that comprises a front exterior microphone that provides a front microphone signal and a rear exterior microphone that provides a rear microphone signal. A processor receives and digitizes the front microphone signal and the rear microphone signal, and provides a front channel signal and a rear channel signal indicative thereof. A filter receives and filters the rear channel signal, and has a cut-off frequency value that provides a high-frequency roll-off and a notch at a notch filter frequency value that is less than the cut-off frequency value, where the filter provides a filtered signal. A first signal indicative of the front channel signal and a second signal indicative of the filtered signal are summed, and a signal indicative of the resultant sum is provided to a transducer that provides an audio signal within the first ear cup indicative of the summed signal.

It is to be understood that the features mentioned above and those to be explained below can be used not only in the respective combinations indicated, but also in other combinations or in isolation.

These and other objects, features and advantages of the invention will become apparent in light of the detailed description of the embodiment thereof, as illustrated in the accompanying drawings.

DESCRIPTION OF THE DRAWINGS

The foregoing and other features of embodiments will become more apparent from the following detailed description of embodiments when read in conjunction with the accompanying drawings. In the drawings, like or identical reference numerals refer to like or identical elements.

DETAILED DESCRIPTION OF THE INVENTION

Figure 8A:
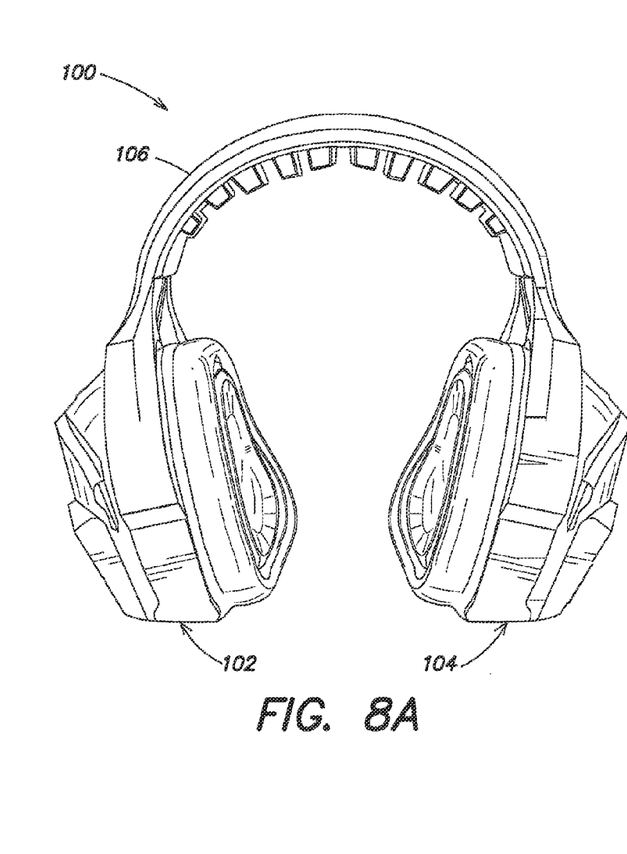
FIGS. 8A and 8B are perspective pictorial illustrations of an electronic hearing protector with quadrant sound localization.
Figure 8B:
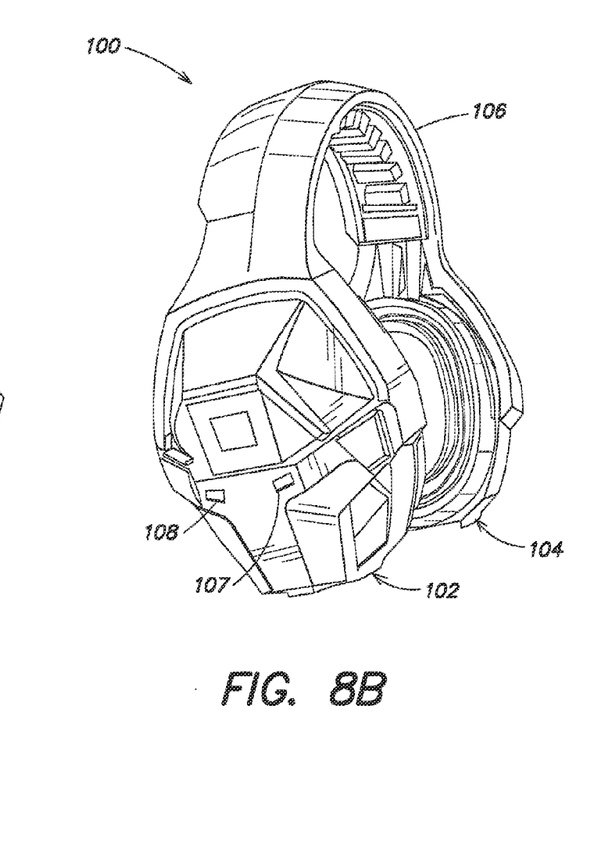

FIGS. 8A and 8B are perspective pictorial illustrations of an electronic hearing protector/headset 100, which includes a first ear cup assembly 102, a second ear cup assembly 104 and a head band 106 that interconnects the first and second ear cup assemblies 102, 104. The first ear cup assembly 102 includes a first front microphone assembly 107 and a first rear microphone assembly 108. The second ear cup assembly 104 includes a second front microphone assembly and a second rear microphone assembly (not shown). Each of the microphone assemblies may include an array microphone comprising a plurality of omnidirectional microphones. Alternatively, directional microphones may also be used.

Figure 9:
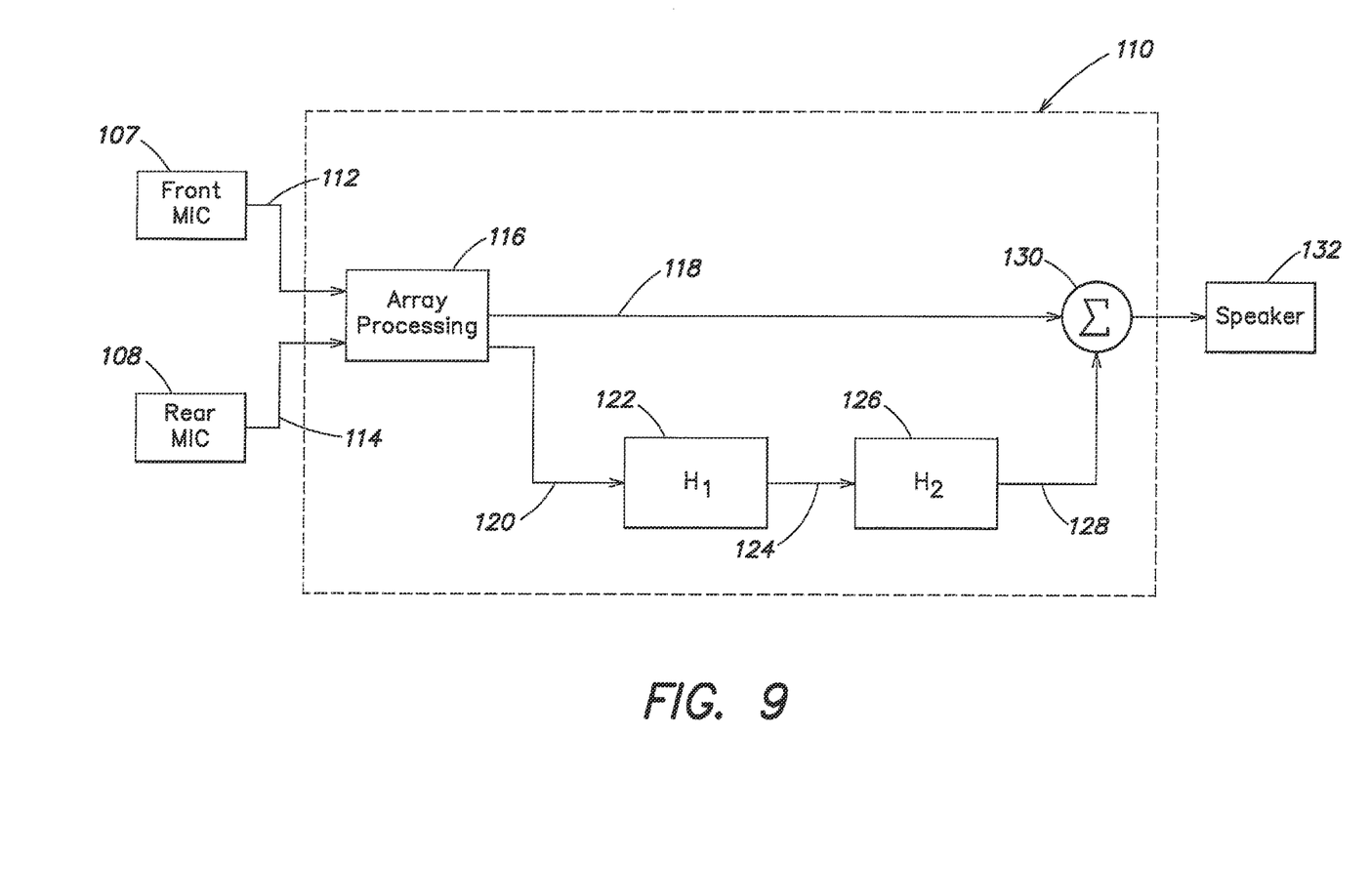
FIG. 9 is a block diagram illustration of signal processing associated with at least one of the ear cup assemblies of the electronic hearing protector illustrated in FIGS. 8A-8B.

FIG. 9 is a block diagram illustration of signal processing 110 associated with at least one of the ear cup assemblies 102, 104 (FIGS. 8A and 8B). The front microphone assembly provides a front microphone signal on a line 112 and the rear microphone assembly provides a rear microphone signal on a line 114. Array processor 116 processes the front and rear microphone signals and provides a front channel signal on a line 118 and a rear channel signal on a line 120. In general, the array processor is configured and arranged as a delay and subtract beamformer. To provide the front channel signal on the line 118, the rear microphone signal on the line 114 is delayed by a time equal to the propagation time between the front and rear microphones (typically tens of microseconds), then subtracted from the front microphone signal on the line 112. The resultant difference is provided as the front channel signal on the line 118. To provide the rear channel signal on the line 120, the front microphone signal on the line 112 is delayed by a time equal to the propagation time between the front and rear microphone, and the delayed front microphone signal is subtracted from the rear microphone signal on the line 114. The resultant difference is provided as the rear channel signal on the line 120.

In this embodiment a first filter 122 receives the rear channel signal on the line 120 and provides a first filtered signal on a line 124. In one embodiment the first filter 122 may be configured as a low pass filter having a cut-off frequency value $f_{c1}$. The first filter 122 may be implemented as a biquad filter structure. However, it is contemplated that the first filter may be implemented in other digital filter embodiments, including for example a 1,024 tap FIR filter. One of ordinary skill will appreciate that the filter implementation for the first filter will primarily be based upon the processing power and memory available. In addition, rather than or in addition to a FIR filter, it is contemplated that alternative filter structures may also be used.

The first filtered signal on the line 124 is input to a second filter 126, which provides a second filtered signal on a line 128. The second filter may be configured as a notch filter having a notch filter value $f_{n1}$. In one embodiment the second filter may also be implemented as a biquad. However, as set forth above with respect to the first filter, it is contemplated that the second filter 126 may be implemented a number of different ways based upon the desired signal processing including filtering, and the processing power and memory available to the designer. It is further contemplated that the processing of the first and second filters may be combined into a single filter that provides an output similar to the serially connected first and second filters illustrated in FIG. 9.

The front channel signal on a line 118 and the second filtered signal on a line 128 may be summed by a summer 130, and a signal indicative of the summed signal is output to a speaker 132 located within the ear cup. The output by the speaker 132 provides enhanced audio with sufficient cues to provide the headset wearer with sound localization (e.g., quadrant sound localization).

In one embodiment the first filter 122 may be configured as a low pass filter with a cut-off frequency located at about 12 kHz. The second filter 126 may be configured as a notch filter with a notch at about 4.9 kHz. This embodiment provides spectral cues that allow the headset wearer to determine front-to-back localization of sounds. The first filter H1 and the second filter H2 may be implemented as biquad filters as follows:

$$H1(z) = \frac{0.3 + 0.59z^{-1} + 0.3z^{-2}}{1 + 0.17z^{-2}}$$

$$H2(z) = \frac{0.86 - 1.37z^{-1} + 0.86z^{-2}}{1 - 1.37z^{-1} + 0.71z^{-2}}$$

In another embodiment, the ear cups 102, 104 (FIGS. 8A-8B) each include front and rear microphones, and the headset provides the associated signal processing illustrated in FIG. 9 to the microphone signals from each ear cup to provide enhanced localization.

It is also contemplated that additional processing may be located between the summer 130 and speaker 132. For example, the additional processing may include noise reduction, dynamics processing, equalizing, mixing and/or volume control, et cetera.

Figure 10:
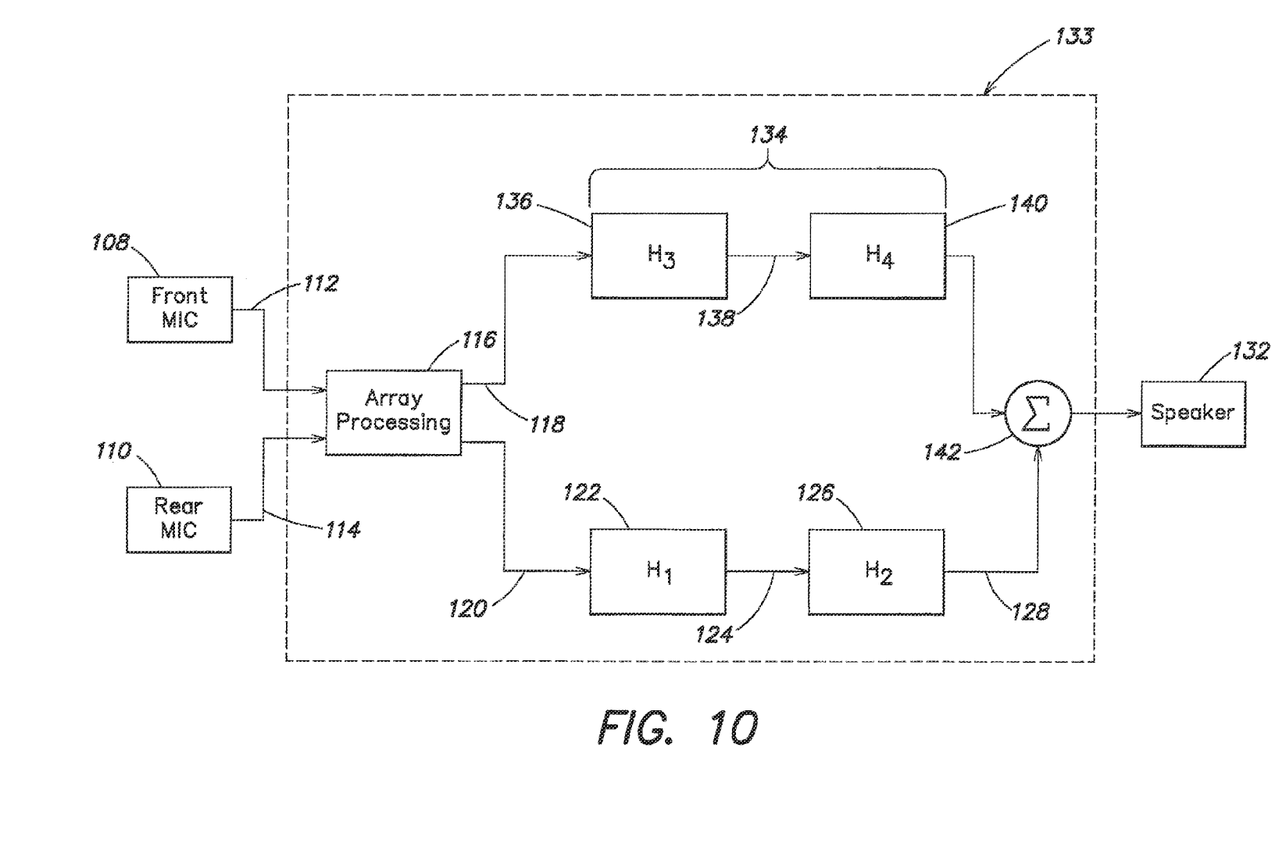
FIG. 10 illustrates another embodiment of signal processing that may associated with at least one of the ear cup assemblies of the electronic hearing protector illustrated in FIGS. 8A-8B.

FIG. 10 illustrates another embodiment of signal processing 133 that may be associated with at least one of the ear cup assemblies 102, 104 (FIG. 10). This embodiment is substantially the same as the embodiment in FIG. 9, with the principal exception that front channel signal path 134 also includes processing to enhance localization and restore some of the naturalness of human hearing. In this embodiment in the front channel signal path includes a first front channel filter H3 136 that receives the front channel signal on the line 118 and provides a first front channel filtered signal on line 138 to a second front channel filter H4 140. In this embodiment summer 142 sums the signal on the line 128 and the output from the second front channel filter 140.

In an embodiment, the first front channel filter H3 136 may be configured as a high-shelf filter and the second front channel filter H4 140 may be configured as a notch filter. Since processing power and memory will be a premium, the first and second front channel filters 136, 140 may be implemented as biquads. Of course, the implementation of the filter will be left to the filter designer based upon the desired system signal processing and the available processing and memory available to implement the filters.

In one embodiment, the first front channel filter H3 136 may be a high-shelf filter with a center frequency fc=1.9 kHz, and the second filter H4 140 may be a notch filter with a notch frequency fn=8.1 kHz, and both may be implemented as biquad filters as follows:

$$H3(z) = \frac{1.39 - 2.59z^{-1} + 1.256z^{-2}}{1 - 1.826z^{-1} + 0.884z^{-2}}$$

$$H4(z) = \frac{0.72 - 0.7z^{-1} + 0.72z^{-2}}{1 - 0.7z^{-1} + 0.43z^{-2}}$$

In order to simulate a head-related transfer function, filters are implemented that mimic the effects of the head and torso on the sound. These filters are applied to the outputs of a microphone array, where beamforming is used to yield forward facing inputs and rearward facing inputs. Because of the limited computing power available in a headset application, the filters may be implemented as digital biquadratic filters. This provides a balance between computational complexity and customizability.

Although discussed in the context of time domain processing, it is contemplated that the filtering may also be performed in the frequency domain. In addition, one of ordinary skill in the art will certainly appreciate that higher order filters may be used. Rather than serially connected filters as illustrated in FIGS. 9 and 10, each channel may use a single filter structure. For example, rather than using serially connected first and second filters 122, 126 illustrated in FIG. 10, a single filter may be used having a notch at about 4.9 kHz and a high frequency roll off at about 12 kHz. The single filter may operate in the time or frequency domains, and may be configured for example as a FIR or IIR filter. The notch may have quality factor Q of about 2.0.

The signal processing 110 and 133 of FIGS. 9 and 10 respectively, may be performed by a microprocessor and complementary memory that stores executable programs that are executed in the microprocessor. One of ordinary skill will appreciate that rather than a microprocessor or a DSP, the signal processing may be performed by an ASIC or a gate array. The memory may include a main memory, a static memory, or a dynamic memory. The memory may include, but is not limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one example, the memory includes a cache or random access memory for the processor. In alternative examples, the memory is separate from the processor, such as a cache memory of a processor, the system memory, or other memory. The memory may include or be an external storage device or database for storing data. The memory is operable to store instructions executable by the processor. The functions, acts or tasks illustrated in the figures or described may be performed by the programmed processor executing instructions stored in the memory. The functions, acts or tasks are independent of the particular type of instructions set, storage media, processor or processing strategy and may be performed by software, hardware, integrated circuits, firmware, micro-code and the like, operating alone or in combination. Likewise, processing strategies may include multiprocessing, multitasking, parallel processing and the like. While a preferred embodiment of the filtering is digital, it is contemplated that analog filtering may also be used.

The electronic hearing protector 100 (FIGS. 8A and 8B) may be used for applications such as shooting ranges, hunting, construction, heavy equipment operators and manufacturing. With respect to application such as a shooting range, the electronic hearing protector headsets protects the wearer from impulse sound such as a gunshots, while allowing the wearer to hear and locate lower-level sound on the range, such as for example instructions from the range officer. In addition, to the signal processing illustrated in FIGS. 9 and 10 to provide sound localization, it is contemplated that the electronic hearing protector may also include additional signal processing to attenuate impulse sound. In addition, each ear cup may include passive impulse noise attenuating features to further protect the hearing of the wearer from damaging impulse noise. It is also contemplated that each ear cup may include a separate volume control so the wearer can independently adjust the speaker volume in each ear cup.

Although the invention has been illustrated and described with respect to several preferred embodiments thereof, various changes, omissions and additions to the form and detail thereof, may be made therein, without departing from the spirit and scope of the invention.

What is claimed is:

1. An electronic hearing protector, comprising:
a front exterior microphone that provides a front microphone signal;
a rear exterior microphone that provides a rear microphone signal;
a single processing unit that performs one or more operations based on the front microphone signal and the rear microphone signal to generate a front channel signal and a rear channel signal;
a first filter that receives the rear channel signal and generates a first filtered signal; and
a summer that receives the front channel signal and the first filtered signal and transmits a summed signal to a transducer that is configured to generate an audio signal based on the summed signal.

2. The electronic hearing protector of claim 1, wherein the first filter has a cut-off frequency value.

3. The electronic hearing protector of claim 2, wherein the first filter comprises a bi-quad filter configured as a low-pass filter.

4. The electronic hearing protector of claim 1, wherein the first filter comprises a bi-quad filter configured as a notch filter.

5. The electronic hearing protector of claim 1, wherein the single processing unit generates the front channel signal based on the front microphone signal and the rear microphone signal.

6. The electronic hearing protector of claim 1, wherein the single processing unit generates the rear channel signal based on the front microphone signal and the rear microphone signal.

7. The electronic hearing protector of claim 1, wherein the single processing unit generates the front channel signal by delaying and subtracting the rear microphone signal from the front microphone signal.

8. An electronic hearing protector, comprising:
a front exterior microphone that provides a front microphone signal;
a rear exterior microphone that provides a rear microphone signal;
a single processing unit that performs one or more operations based on the front microphone signal and the rear microphone signal to generate a front channel signal and a rear channel signal;
a first filter that receives the rear channel signal and generates a first filtered signal;
a second filter that receives the front channel signal and generates a second filtered signal; and
a summer that receives the first filtered signal and the second filtered signal and transmits a summed signal to a transducer that is configured to generate an audio signal based on the summed signal.

9. The electronic hearing protector of claim 8, wherein the first filter comprises a bi-quad filter with a cut-off frequency of about 12 kHz.

10. The electronic hearing protector of claim 8, wherein the first filter comprises a bi-quad filter with a notch frequency of about 4.9 kHz.

11. The electronic hearing protector of claim 8, wherein the second filter comprises a front channel shelf filter.

12. The electronic hearing protector of claim 11, wherein the front channel shelf filter comprises a bi-quad filter with a cut-off frequency of about 1.9 kHz.

13. The electronic hearing protector of claim 8, wherein the second filter comprises a front channel notch filter.

14. The electronic hearing protector of claim 13, wherein the notch filter comprises a bi-quad filter with a notch of about 8.1 kHz.

15. An electronic hearing protector, comprising:
a front exterior microphone that provides a front microphone signal;
a rear exterior microphone that provides a rear microphone signal;
a single processing unit that performs one or more operations based on the front microphone signal and the rear microphone signal to generate a front channel signal and a rear channel signal;
a filter that receives the rear channel signal and generates a filtered signal; and
a summer that receives the filtered signal and a first signal based on the front channel signal and transmits a summed signal to a transducer that is configured to provide an audio signal based on the summed signal.

16. The electronic hearing protector of claim 15, wherein the filter has a cut-off frequency value that provides a high-frequency roll-off.

17. The electronic hearing protector of claim 15, wherein the first signal comprises the front channel signal.

18. The electronic hearing protector of claim 15, further comprising:
a front channel shelf filter that receives the front channel signal and generates a front channel filtered signal; and
a front channel notch filter that receives the front channel filtered signal and generates the first signal.

19. The electronic hearing protector of claim 18, wherein the front channel shelf filter has a cut-off frequency value of about 1.9 kHz, and the front channel notch filter has a notch filter frequency value of about 8.1 kHz.

20. The electronic hearing protector of claim 15, where the filter has a first cut-off frequency value of about 12 kHz and a notch filter frequency value of about 4.9 kHz.

* * * * *